United States Patent [19]

Padovani

[11] Patent Number: 5,315,672
[45] Date of Patent: May 24, 1994

[54] FIBER OPTIC CHEMICAL SENSOR

[75] Inventor: Francois A. Padovani, Westwood, Mass.

[73] Assignee: Texas Instruments Incorporated, Dallas, Tex.

[21] Appl. No.: 764,257

[22] Filed: Sep. 23, 1991

[51] Int. Cl.$^5$ .......................... G02B 6/02; G02B 6/12
[52] U.S. Cl. .................................. 385/12; 250/227.11; 257/82
[58] Field of Search ...................... 385/12, 13, 14, 123, 385/126–128; 250/227.11, 227.14–227.19, 227.23, 227.28, 231.1; 357/72, 73

[56] References Cited

U.S. PATENT DOCUMENTS

| | | | |
|---|---|---|---|
| 4,523,092 | 6/1985 | Nelson | 250/227.23 |
| 4,755,667 | 7/1988 | Marsoner et al. | 250/227.10 |
| 4,824,206 | 4/1989 | Klainer et al. | 385/12 |
| 4,846,548 | 7/1989 | Klainer | 385/12 |
| 4,872,759 | 10/1989 | Stich-Baumeister | 356/432 |
| 4,892,374 | 1/1990 | Ackerman et al. | 385/14 X |
| 4,913,519 | 4/1990 | Klainer et al. | 250/227.28 X |
| 4,940,328 | 7/1990 | Hartman | 356/345 |
| 4,984,863 | 1/1991 | Parriaux et al. | 385/14 X |

FOREIGN PATENT DOCUMENTS

| | | | |
|---|---|---|---|
| 0263805 | 4/1988 | Fed. Rep. of Germany | G01N 21/77 |
| 0298333 | 11/1989 | Fed. Rep. of Germany | G01N 21/77 |
| WO-A-8908273 | 8/1989 | PCT Int'l Appl. | G02B 6/02 |
| WO-A-9205429 | 4/1992 | PCT Int'l Appl. | G01N 21/77 |

OTHER PUBLICATIONS

Patent Abstracts of Japan, vol. 4, No. 39 (P-004) 28 Mar. 1980 & JP-A-55 012 463 (NEC) 29 Jan. 1980.
ISA Transactions, vol. 28, No. 2, 1989, Pittsburgh US, pp. 71–77.

*Primary Examiner*—Akm E. Ullah
*Attorney, Agent, or Firm*—Russell E. Baumann; Richard L. Donaldson; René E. Grossman

[57] ABSTRACT

A fiber optic sensor for detecting the presence or concentration of particular chemical or biological species in a zone to be monitored has light-emitting and detecting elements such as a gallium arsenide light-emitting diode and a Schottky diode light detector provided in a semiconductor body, and has an optical fiber formed in situ on a surface of the body to conduct light from the light-emitting diode to the detector. The fiber has a long light-transmitting core of a material such as silicon dioxide deposited on a semiconductor body surface and defined by photolithographic techniques and has a cladding deposited over and around the core of a material of relatively lower refractive index than the core. The cladding material reacts when contacted by the particular chemical or biological species to produce measurable changes in transmission of light through the fiber so that the detector provides an electrical signal representative of the presence or concentration of the species.

16 Claims, 3 Drawing Sheets

FIBER OPTIC CHEMICAL SENSOR

BACKGROUND OF THE INVENTION

The field of the invention is that of sensors for detecting the presence or concentration of particular chemical or biological species and the invention relates more particularly to a novel and improved sensor utilizing an optical fiber.

Certain known fiber optic chemical sensors as shown in U.S. Pat. Nos. 4,824,206 and 4,846,548 use an optical fiber having a core of light-transmitting material and a cladding of relatively lower refractive index than the core. The fiber receives light within one end of its core and transmits the light along the length of the core by total internal reflection from an interface located within the fiber between the fiber core and cladding. A light sensor receives the light at the opposite end of the core and provides an electrical signal corresponding to the amount of light transmitted by the fiber. The cladding is formed of a material which reacts when contacted by a particular chemical or biological species to produce a measurable change in light transmission by the fiber, whereby a change in the signal provided by the detector is representative of the presence or concentration of the species in contact with the cladding. In one known sensor, the light source and detector comprise light-emitting and detecting diodes provided in a common semiconductor body and the optical fiber is fitted into a channel provided in the body to conduct light from the source to the detector. In such known devices it is difficult to furnish and receive light to and from the fiber in a consistent manner and it is difficult to arrange the device to monitor a zone for the presence of the particular chemical or biological species.

BRIEF SUMMARY OF THE INVENTION

It is an object of the invention to provide a novel and improved fiber optic chemical or biological species sensor; to provide such a sensor which is characterized by increased efficiency of operation; and to provide such a sensor of a rugged and economical construction which is easily mounted to monitor a zone for the presence of the species. It is also an object of the invention to provide novel and improved methods for making the fiber optic sensor of the invention.

Briefly described, the novel and improved fiber optic sensor of the invention comprises a semiconductor body having a light-emitting source or element such as a gallium arsenide light-emitting diode provided at a surface of the semiconductor body in spaced relation to a light-detecting element such as a Schottky or P-N junction diode formed at the same body surface. A light-transmitting optical fiber is formed in situ on a surface of the semiconductor body optically coupled to the light-emitting and detecting elements to conduct light with improved efficiency from the light source to the detector. In forming the optical fiber, a coating of a material such as strontium or rubidium fluoride of relatively low refractive index is preferably provided on the semiconductor body by a conventional vapor deposition technique or the like to cover the noted body surface between the light-emitting and detecting elements, and a layer of a light-transmitting material such as silicon dioxide of relatively higher refractive index than the coating is deposited over the coating by a corresponding deposition procedure. Selected portions of the coating and light-transmitting layer are then defined by conventional photolithographic techniques and other portions are removed by etching to leave a strip of the light-transmitting material, separated from the body by a correspondingly shaped strip of the lower refractive index coating, to serve as a light-transmitting core piece of an optical fiber extending from the light-emitting element to the detecting element. A selected material also of relatively lower refractive index than the core piece is then deposited on the semiconductor body surface over and around the core piece to cooperate with the coating strip to serve as an optical fiber cladding. That is, the selected material cooperates with the coating and core piece defined on the semiconductor body to constitute an optical fiber formed in situ on the body optically coupled to the emitting and detecting elements to conduct light between the light-emitting and detecting elements. The cladding material is selected to be a material which reacts when contacted by a particular chemical or biological species to change transmission of light through the fiber. In that arrangement, the optical fiber is easily and efficiently coupled to the light-emitting and detecting elements and the sensor is adapted to be easily mounted to dispose the optical fiber cladding material where it is easily exposed to particular chemical or biological species in a zone to be monitored.

In a preferred embodiment of the invention, the light-emitting and detecting elements are disposed on peripheral and central portions respectively of the semiconductor body surface and an optical fiber of substantial length is formed in a spiral configuration extending between the light-emitting and detecting elements. In one preferred embodiment, a second light-detecting element is provided on the semiconductor body and a second optical fiber is formed in situ on the body between the light-emitting element and a second detector. The cladding of the second fiber is preferably made of a chemically or biologically unreactive material of lower refractive index than the core, or if desired the second fiber corresponds to the first fiber but is arranged at a location to be shielded from the zone to be monitored, thereby to provide a comparison electrical signal from the second detecting element to be representative of the light source in the sensor. In a preferred embodiment, an integrated circuit is also accommodated in the semiconductor body to program a test sequence, to compare signals from the two elements and/or to condition the signal from the detecting element or elements and to provide a sensor output at the desired signal level.

DESCRIPTION OF THE DRAWINGS

Other objects, advantages and details of the novel and improved fiber optic sensor of the invention and of the methods of manufacture provided by the invention appear in the following detailed description of preferred embodiments of the invention, the detailed description referring to the drawings in which.

DESCRIPTION OF THE PREFERRED EMBODIMENTS

Figure 1:
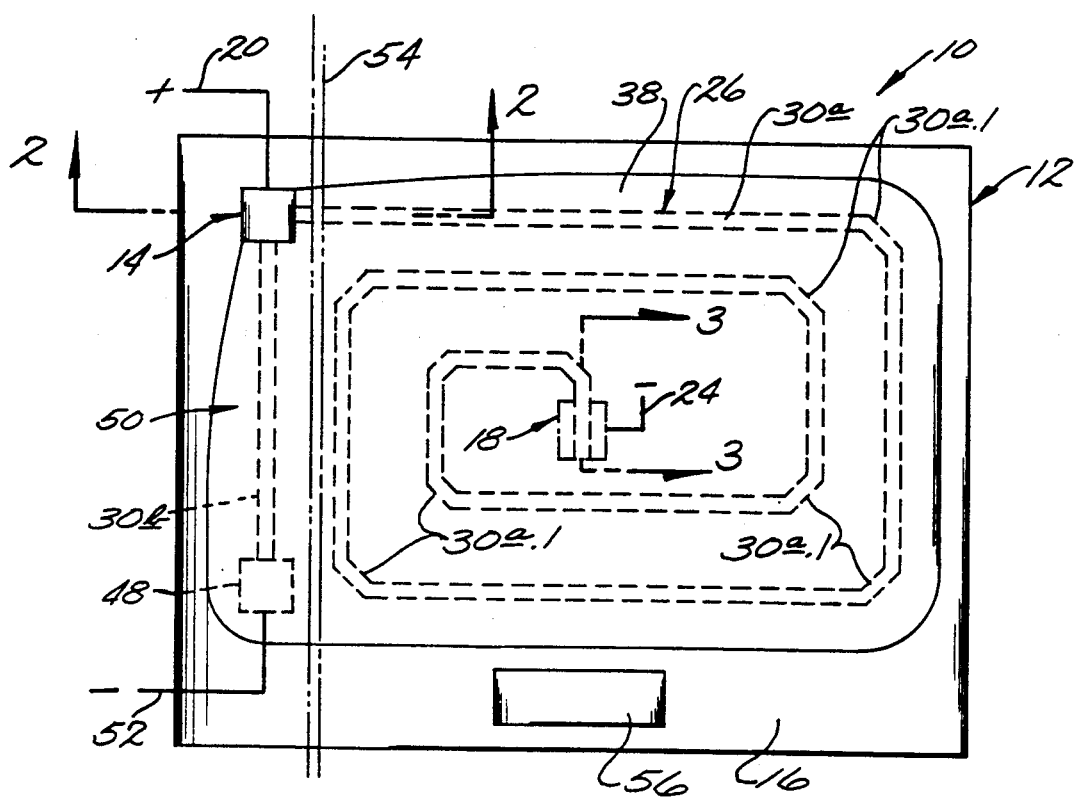
FIG. 1 is a plan view of the fiber optic sensor of the invention.

Referring to the drawings, the novel and improved fiber optic chemical sensor 10 of the invention comprises a semiconductor body 12 having a light-emitting element 14 accommodated on a body side surface 16 and having a light-detecting element 18 also arranged on the body in spaced relation to the element 14.

Preferably the light-emitting element comprises a gallium arsenide P-N junction while the light-detecting element comprises another P-N junction or a Schottky diode depending on the type of semiconductor materials being utilized. In one preferred embodiment, where the semiconducting body is formed of gallium arsenide, the light-emitting element comprises a gallium arsenide P-N junction and the light-detecting element comprises a Schottky diode. In another preferred and less expensive embodiment, where the semiconductor body is formed of silicon, a gallium arsenide light-emitting diode having P-N junction is deposited on the silicon body in any conventional manner and the light-detecting element comprises a Schottky diode or a P-N junction formed in the silicon body. In that regard, the P-N junction in the gallium arsenide diode has an energy level considerably higher than the internal barrier height of a Schottky diode, gallium arsenide having an energy gap of $1.38^{ev}$ at 20° C. while a Schottky diode has a built-in barrier of $0.8^{ev}$.

Figure 2:
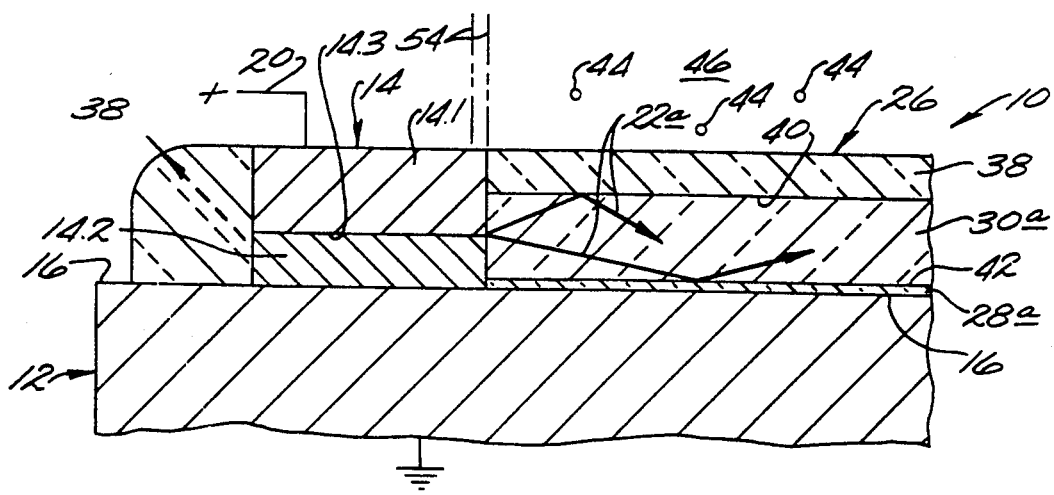
FIG. 2 is a partial section view to enlarged scale along line 2—2 of FIG. 1.
Figure 3:
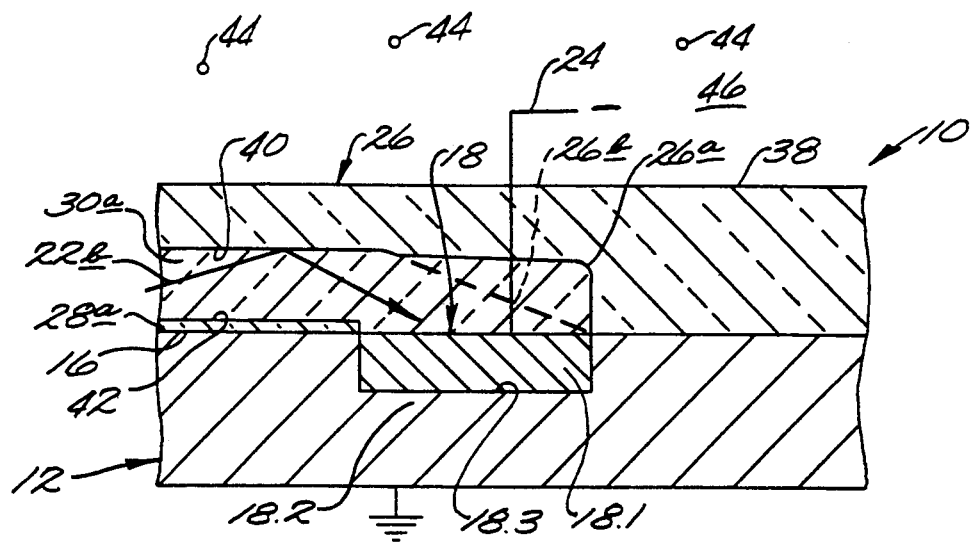
FIG. 3 is a partial section view to enlarged scale along line 3—3 of FIG. 1.

In the preferred embodiment of the invention as shown in FIGS. 1-3, the semiconductor body 12 comprises silicon semiconducting material and the light-emitting element 14 is formed on the body by deposition of two gallium arsenide layers 14.1, 14.2 of opposite conductivity type in superimposed relation to each other on a portion of a body surface 16 to provide a gallium arsenide light-emitting diode having a P-N junction 14.3 disposed or extending parallel to and above the body surface 16. The element 14 is responsive to energy input as diagrammatically indicated by the power input lead 20 in FIG. 2 to emit light laterally from that P-N junction as indicated by the arrows 22a. The light-detecting element 18 comprises a P-N junction 18.3 formed in the body by a region 18.1 of silicon material of one conductivity type provided in a silicon body region 18.2 of a different conductivity type. The P-N junction 18.3 is responsive to light directed thereon as indicated by the arrows 22b in FIG. 3 to provide an electrical output signal corresponding to the incident light via an output lead 24 as is diagrammatically indicated in FIG. 3.

In accordance with the invention an optical fiber means 26 is formed in situ on the body 12 in optically coupled relation to each of the light-emitting and detecting elements 14 and 18 to receive light from the source 14 and conduct it efficiently to the detector 18 so that the output signal at the lead 24 corresponds to the light transmitted or conducted to the detector. The cladding of the optical fiber is selected in well known manner to react with particular chemical or biological species to change the transmission of light by the fiber. In that way, when the optical fiber of the sensor is located in a zone to be monitored, the output signal of the lead 24 corresponds to the presence or absence of the species in the zone and/or to the concentration of the species in the zone.

Figure 4A:
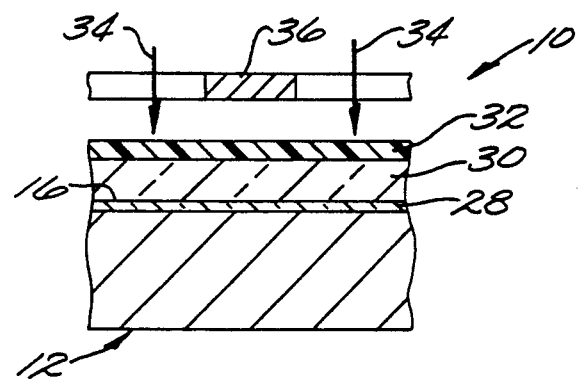
FIGS. 4A–C are partial section views along a horizontal axis illustrating steps in the method for forming a fiber optic sensor according to the invention.
Figure 4B:
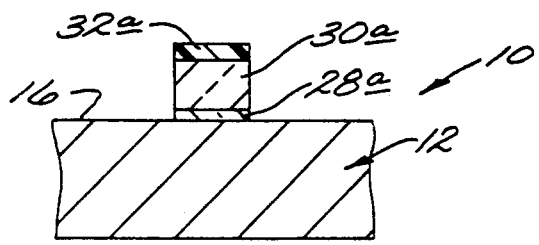
Figure 4C:
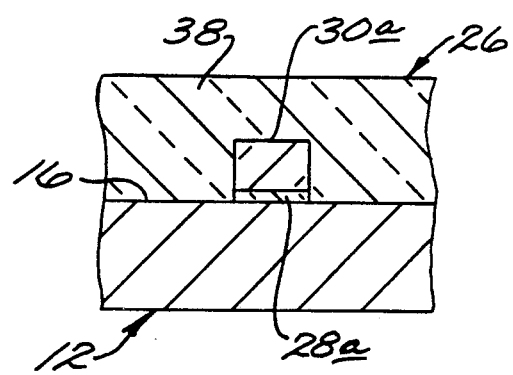

In a preferred method for forming the optical fiber 26 in situ as shown in FIGS. 4A-C, a coating 28 of a material such as strontium or rubidium fluoride or any other suitable fluoride or the like of relatively low refractive index is deposited on the body surface 16 by any conventional vapor deposition technique or the like to adhere to the body and to cover the area of the surface located between the light-emitting and detecting elements. A layer 30 of a light-transmitting material such as silicon dioxide or the like of relatively higher refractive index than the coating 28 is deposited on top of the coating in adherent relation to the coating. A layer of a photoresist material 32 is formed over the light-transmitting and coating layers as shown in FIG. 4A.

After exposure of the photoresist to light 34 by a mask 36 as is shown diagrammatically in FIG. 4A, portions of the light-transmitting layer and coating are removed by etching or in other conventional manner as indicated in FIG. 4B to leave a strip 30a of the light-transmitting layer material, as well as an underlying strip 28a of the coating material, defined on the semiconductor body 12 extending between the light-emitting and detecting elements 14 and 18. In that arrangement, the strip 30a is adapted to form the core piece of the optical fiber 26. The remainder 32a of the photoresist is then removed in conventional manner. As will be understood, any other conventional photolithographic technique or the like is also adapted to be used in defining the core piece 30a on the semiconductor body within the scope of the invention.

A selected material 38 of relatively lower refractive index than the light-transmitting material 30 is then deposited on the body surface 16 over and around the lateral surfaces of the core piece 30a in adherent relation to the core 30a and to the body surface 16 to serve as cladding for the core of the optical fiber 26 as shown in FIG. 4C. In that arrangement, the cladding material 38 cooperates with the core piece 30a and the coating strip 28a to form the optical fiber 26 in situ on the body 12 optically coupled with the elements 14 and 18 so that light 22a, 22b emitted from the element 14 is conducted through the fiber by total internal reflection from the interfaces 40 and 42 located within the fiber between the core piece 30a of relatively high refractive index and the cladding and coating materials respectively of relatively lower refractive index surrounding the core piece as shown in FIGS. 2-3 In that way, the light is conducted to the detector element 18 to provide an output signal at the lead 24 corresponding to the light conducted to the detector. The cladding 38 is shown covering less than the full body surface for clarity of illustration but covers the full surface 16 if desired.

The cladding material 38 is selected in known manner to be a material which reacts with particularly chemical or biological species 44 when contacted by the species in a zone 46 to be monitored to produce measurable change in the transmission of light through the fiber 26, whereby the output signal at the lead 24 correspondingly changes and indicates the presence and/or concentration of the species in the zone. As such reactive optical fiber cladding materials are well known as shown in U.S. Pat. No. 4,846,548, U.S. Pat. No. 4,824,206 and U.S. Pat. No. 4,913,519, the disclosures of which are incorporated herein by this reference, the core cladding and coating materials used in the sensor 10 are not further described herein and it will be understood that the cladding and coating materials are selected to have refractive indices which are low relative to the refractive index of the core piece material in the absence of a particular chemical or biological species in the zone so that light is normally conducted through the fiber 26 to the element 18 but so that the transmission of the light is changed in the presence of the species to provide a change in the signal related to the presence of the species.

In a preferred embodiment of the invention, the light source 14 is disposed at a peripheral location on the body surface 16 as shown in FIG. 1 and the detector 18 is provided with a central location. In that arrangement, the optical fiber 26 is provided in a spiral configuration around the detector to provide a convoluted light path of substantial length through the fiber between the light source and detector. Where the optical fiber configuration is somewhat rectilinear as illustrated in FIG. 1, the core piece 30a is preferably provided with obliquely disposed corners 30a.1 to assist in reflecting light along the length of the optical fiber. Alternately the fiber is arranged in a circular configuration to facilitate transmission of light through the fiber as will be understood. In an expensive sensor, the end 26a of the core of the optical fiber is arranged as shown in FIG. 3 to direct light 22b from the fiber interface 40 onto the P-N junction 18.3. Preferably the P-N junction of the element 18 has a relatively greater length than width and the width corresponds to the fiber width. The length is oriented in alignment with the longitudinal axis of the fiber core end 26a and the length is selected to permit transmission of substantially all of the transmitted light to the P-N junction as the fiber extends over the length of the P-N junction in the element 18. Alternately the fiber core end is adapted to be shaped as indicated diagrammatically at 26b in FIG. 3 to facilitate directing light onto the P-N junction 18.3.

In a preferred embodiment, a second light-detecting element is provided on the body 12 and a second optical fiber 50 is formed on the body conducting light from the source 14 to the second detector along the second fiber, whereby the second detector is adapted to provide an output signal from a lead 52 as is diagrammatically illustrated in FIG. 1. Preferably a second core piece 30b with an underlying coating piece (not shown) corresponding to coating piece 28a is deposited on the body surface 16 and the cladding 38 is extended over and around the core piece 30b. Preferably the core pieces 30a and 30b are formed at the same time. In that way, the detector 48 is adapted to provide an output signal at lead 52 corresponding to the light output of the source for comparison with the output signal provided at the lead 24 both in the presence and absence of particular reactive species 44 in the zone to be monitored. Where the second detector is used, the cladding 38 provided on the core piece 30b is preferably selected to be of a material which is like that of the core piece in that it is unreactive with respect to the noted chemical or biological species so that the signal provided by second detector is substantially the same whether in the presence or absence of the species. Alternately, the sensor is preferably mounted so that the second optical fiber 50 is not exposed in the zone 46 to be monitored and is shielded from reaction with the particular species 44 by a barrier as is diagrammatically indicated at 54 in FIG. 1.

Preferably a signal-conditioning integrated circuit is also incorporated in the semiconductor body as is diagrammatically indicated at 56 in FIG. 1 for regulating operation of the light-emitting and detecting elements in any conventional manner. That is, as will be understood, the circuit 56 is adapted to receive power input via the lead 20 to operate the light source 14 in any continuous or sequential manner as may be desired and also to operate the detector or detectors 18 and 48 to provide desired output and comparison signals with appropriate amplification and the like as may be desired.

The sensor 10 as thus described is easily and economically made with consistently reproducible operating characteristics in a variety of embodiments to detect the presence of particular different chemical or biological species based on selection of the core, coating and cladding materials as above-described. The sensor is easily mounted in a barrier or wall 54 of a zone to be monitored as shown in FIG. 2 so that the reactive cladding material 38 is easily exposed in a consistent way to contact with the species 44 whose presence or absence is to be detected in the zone 46.

Figure 5:
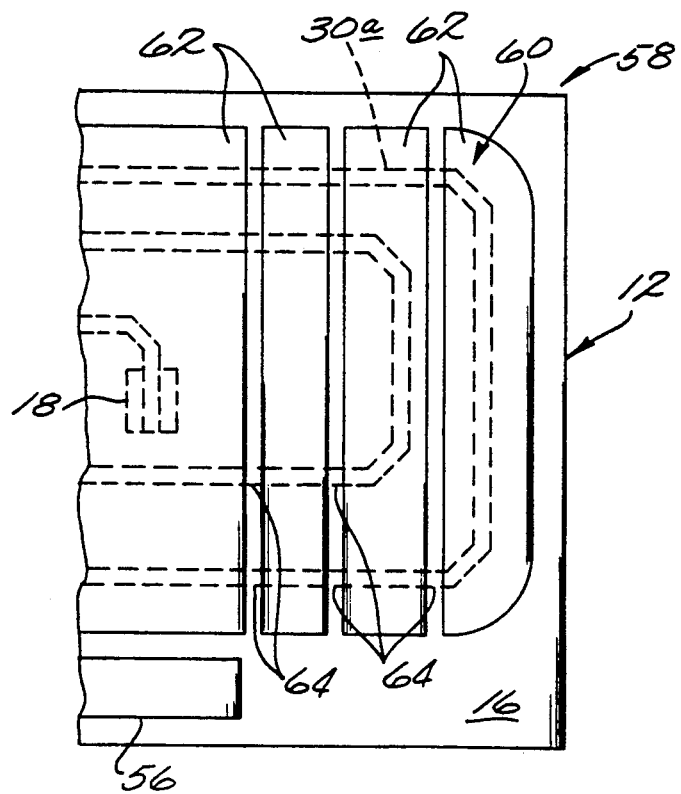
FIG. 5 is a partial plan view similar to FIG. 1 illustrating an alternate preferred embodiment of the invention.

In another embodiment of the invention as shown at 58 in FIG. 5, wherein corresponding components are identified with corresponding reference numerals, an optical fiber 60 is formed in situ on a surface 16 of a semiconductor body between light emitting and detecting elements. The optical fiber 60 includes a core piece 30a together with an underlying coating strip (not shown) as previously described, and a cladding material 62 is deposited on the body surface, preferably by use of a mask or the like (not shown), so that the cladding covers some portions of the core piece but so that portions of the core piece as indicated at 64 in FIG. 2 are left exposed. The cladding is preferably formed of a material having a refractive index substantially the same as ice (1.3049) at or near 0° C. while the core piece 30a is formed of a light-transmitting material having a refractive index greater than the cladding material but less than that of water at a level near 0° C. (1.3354). Preferably the spaces 64 are small enough to tend to hold water therein. In that arrangement, the presence of water in spaces 64 between portions of the cladding material substantially prevents light transmission by the fiber 60 but when the water freezes to ice, the fiber conducts light to the element 18 to provide an output signal corresponding to the presence of the ice.

It should be understood that although particular embodiments of the sensor and methods of this invention have been described by way of illustrating the invention, the invention includes all modifications and equivalent of the disclosed embodiments falling within the scope of the appended claims.

I claim:

1. A sensor comprising a body of semiconductor material accommodating a light-emitting and light-detecting element, an optical fiber formed in situ on the body in optically coupled relation to the elements for normally transmitting light from the light-emitting element to the light-detecting element to provide an electrical signal corresponding to the light, the optical fiber having a core for transmitting the light and having cladding means around at least a portion of the core responsive to a particular chemical or biological species to change light transmission of the optical fiber for regulating the signal to be representative of presence of the species, and an additional light-detecting element accommodated by the body and having an additional optical fiber formed in situ on the body in optically coupled relation to the light-emitting element and the additional light-detecting element to transmit light to the additional light-detecting element for providing a comparison electrical signal representative of the light output of the light-emitting element.

2. A sensor for detecting the presence of a particular chemical or biological species in a zone to be monitored comprising a body of semiconductor material having a light-emitting element and a light-detecting element accommodated at a surface of the body, an optical fiber on the body surface in optically coupled relation to the elements at respective opposite ends of the optical fiber for normally transmitting light from the light-emitting element to the light-detecting element to provide an electrical signal corresponding to the light, the optical fiber having a core formed on the body in adherent relation to the body surface to define a convoluted light path between the elements and having a cladding material disposed around at least a portion of the core in adherent relation to the core and body surface, the cladding material being selected to react with a particular chemical or biological species to produce measurable change in transmission of light through the optical fiber for regulating the signal to be representative of the presence of the species, and an additional light-detecting element accommodated by the body and having an additional optical fiber formed in situ on the body in optically coupled relation to the light-emitting element and the additional light-detecting element to transmit light to the additional light-detecting element for providing a comparison electrical signal representative of the light output of the light-emitting element.

3. A sensor according to claim 2 wherein a coating of a material of relatively lower refractive index than the core is deposited on the body surface between the core and body surface in adherent relation to the core and body surface, and the cladding material is disposed on the body surface over and around the core.

4. A sensor according to claim 2 wherein the light-emitting element comprises a gallium arsenide P-N junction.

5. A sensor according to claim 4 wherein the semiconductor body comprises gallium arsenide having a gallium arsenide light-emitting diode formed therein and having a Schottky diode light-detecting element formed therein.

6. A sensor according to claim 4 wherein the semiconductor body comprises silicon semiconducting material having a gallium arsenide light-emitting diode deposited thereon.

7. A sensor according to claim 6 wherein the light-detecting element comprises a P-N junction incorporated in the silicon semiconductor body.

8. A sensor according to claim 6 wherein the light-detecting element comprises a Schottky diode incorporated in the silicon semiconductor body.

9. A chemically or biologically responsive sensor comprising a body of semiconductor material, a light-emitting element embodying a gallium arsenide P-N junction incorporated in the body spaced from a central portion of a surface of the body, a first light-detecting element incorporated in the central portion of the surface of the body, a first optical fiber formed in situ on the body surface defining a spiral light-transmitting path around the central portion of the body surface extending between the light-emitting element and the first light-detecting element, the first optical fiber embodying a core for transmitting light to the first detecting element to provide a first electrical signal and having a reactive layer around at least a portion of the core which reacts with a predetermined chemical or biological species to produce measurable changes in transmission of light through the first optical fiber when the reactive layer is contacted by the predetermined species for regulating the electrical signal to be representative of the presence of the species, a second light-detecting element incorporated in the body surface outside the spiral path, and a second optical fiber formed in situ on the body surface between the light emitting element and the second detecting element transmitting light to the second light-detecting element to provide a second electrical signal representative of the light-emitting element.

10. A sensor according to claim 9 having a signal-conditioning circuit integrated in the semiconductor body comparing the first and second signals to provide an output signal precisely representative of the presence of the predetermined species.

11. A sensor according to claim 9 wherein the light-emitting element comprises two layers of gallium arsenide material disposed in superimposed relation on the body surface between respective ends of the first and second optical fibers to form a light-emitting diode and to provide a P-N junction thereof disposed parallel to the body surface for emitting light laterally from the gallium arsenide layer into the optical fibers.

12. A sensor according to claim 9 wherein the light detecting elements are incorporated in the semiconductor body beneath ends of the respective fibers, each light detecting element embodying a P-N junction of relatively greater length than width oriented in the body with the length of the junction extending beneath a corresponding length of the fiber at said end of the fiber.

13. A method for forming an optical fiber sensor comprising the steps of providing a body of semiconductor material incorporating a light-emitting element, a light-detecting element and an additional light-detecting element, depositing a first layer of a coating material of a first index of refraction on a surface of the body between the light-emitting element and each of the light-detecting elements in adherent relation to the body, depositing a second layer of a light-transmitting material of a refractive index relatively greater than that of the first layer coating material on said coating material in adherent relation to the coating material, selectively removing at least a portion of at least the second layer material to define a narrow strip of the light-transmitting material extending along a convoluted path between both the light-emitting element and light-detecting element and the light-emitting element and the additional light-detecting element, and depositing a layer of cladding material of relatively lower index of refraction than that of the light-transmitting second layer material over and around at least a portion of the narrow strip in adherent relation to the body surface and the strip to form optical fibers optically coupled to the elements to transmit light from the light-emitting element to the light-detecting element to provide an electric signal corresponding to the transmitted light, the cladding material being selected to react with a particular chemical or biological species to produce measurable change in the transmitted light so that the electrical signal indicates the presence of the species, and to transmit light from the light-emitting element to the additional light-detecting element to provide an additional electric signal representative of the light output from the light-emitting element.

14. A method according to claim 13 wherein the semiconductor body incorporates a gallium arsenide light-emitting diode.

15. A method according to claim 136 wherein the semiconductor body comprises a body or silicon semiconducting material having a pair of light-detecting diodes incorporated therein and a gallium arsenide light-emitting diode is deposited on the body.

16. A method according to claim 15 wherein the light-detecting diodes comprise Schottky diodes.

* * * * *